United States Patent [19]

Arnold

[11] Patent Number: 5,017,186

[45] Date of Patent: May 21, 1991

[54] DEVICE AND METHOD FOR MAINTAINING STERILITY OF MULTI-DOSE MEDICAMENT VIALS

[76] Inventor: Victor A. Arnold, 3715 N. 12th Pl., Phoenix, Ariz. 85014

[21] Appl. No.: 378,063

[22] Filed: Jul. 11, 1989

[51] Int. Cl.[5] .......... A61M 31/00

[52] U.S. Cl. .......... 604/48; 604/51; 141/63; 141/48

[58] Field of Search .......... 141/37, 63, 47-48, 141/319-322; 604/187, 189, 199, 403, 405, 415-416

[56] References Cited

U.S. PATENT DOCUMENTS 3,620,265 11/1971 Strople et al. .......... 141/63 X
3,993,063 11/1976 Larrabee .......... 128/215
4,518,387 5/1985 Murphy et al. .......... 604/187
4,766,908 8/1988 Clement .......... 128/765
4,799,926 1/1989 Haber .......... 604/187
4,921,020 5/1990 Pamper .......... 141/20

*Primary Examiner*—C. Fred Rosenbaum
*Assistant Examiner*—Corrine Maglione

[57] ABSTRACT

The disclosure of this application is directed to a medicament injection adjunct which provides a source of sterile air for loading into a medicament syringe prior to use of the syringe for withdrawing liquid medicament from a multi-dose vial. The disclosure also describes the sequence of steps involved in loading the syringe with sterile air. Embodiments involving inclusion of the adjunct in a tandem medicament package and also use of the adjunct in hospital wards or outpatient areas are also described.

10 Claims, 2 Drawing Sheets

DEVICE AND METHOD FOR MAINTAINING STERILITY OF MULTI-DOSE MEDICAMENT VIALS

BACKGROUND OF THE INVENTION

The present invention relates generally to a tube or reservoir which provides a source of clean air for injection into a multi-dose medicament vial prior to withdrawing medicament from the vial for injection into a patient. The invention also relates to a method for loading sterile air into the barrel of a syringe prior to use of the syringe to withdraw medicament from a multi-dose vial.

Liquid medication which is to be injected by needle is often sold in multi-dose containers. In some cases (e.g., insulin), as many as 50 or 60 doses or shots are contained in a single vial. The vials are fitted with a rubber diaphragm, and when a dose is to be administered, the needle of a syringe is pushed through the rubber membrane and the proper amount of liquid medicament is withdrawn for injection into the patient.

Since the vial is airtight, withdrawal of liquid medicament creates a partial vacuum inside the vial, and, after a few doses have been withdrawn, the vacuum becomes enough of a factor to make it difficult to withdraw any further doses. To compensate for this, the standard practice, each time a dose is to be administered, is to inject a quantity of air into the vial first, and then withdraw the medication. As described by Sorensen et al in Basic Nursing, page 949 et seq. (W. B. Saunders Company, Philadelphia, 1979), the standard procedure includes the following steps:

1. Cleanse the stopper of the vial with alcohol or Betadine.
2. Draw into the syringe an amount of atmospheric air about equal in volume to the dose to be withdrawn from the vial.
3. Push the syringe needle through the stopper of the vial, and inject air into the vial. Then withdraw the amount of medication needed.
4. Proceed with injection of the patient.

A source of potential problems in the above standard procedure is that, if the atmospheric air should be contaminated, the contamination is incorporated in the dose of medication and is injected through the skin (normally the body's first line of defense against infection). Pathogens in the atmospheric air are thus introduced directly into the body tissues or blood, where they can cause serious infections. The problem is aggravated if the liquid medication (e.g., NPH insulin) contains suspended solids and must be shaken before the dose is withdrawn from the vial, and shaking is a common practice even when not necessary. In any case, shaking causes the contaminated air to be thoroughly mixed with the medicament. The problem is especially aggravated after 30 or 40 shots of contaminated air have been injected into the vial.

It is an object of the present invention to provide a device and a method for overcoming the above-mentioned problems associated with the injection of atmospheric air into medicament vials.

It is a further object of the invention to provide a specially designed medicament injection adjunct for furnishing the air to be injected into medicament vials.

It is a still further object of the invention to provide a sequence of method steps resulting in loading a medical syringe with sterile air and using such air to obtain a dose of medication for parenteral administration to patients.

Other objects and advantages will become apparent as the specification proceeds.

SUMMARY OF THE INVENTION

The present invention relates to a medicament injection adjunct as a vessel containing a charge of sterile air under low pressure, said vessel having substantially rigid, air impermeable walls and an aperture which is sealed by a puncturable, self-sealing closure, through which the needle of a syringe may be inserted to withdraw sterile air.

The invention also relates to a method of administering liquid medication to a patient by injection through the skin, comprising the steps of loading sterile air into the barrel of a syringe, pushing the syringe needle distally through the septum of a medicament vial, expelling air from the barrel of said syringe into the interior of said vial, moving the syringe plunger proximally to withdraw the desired dosage of medicament from said vial, and injecting said dosage through the skin of said patient.

An alternative embodiment of the invention relates to a tandem medicament injection package comprising a vial of injectable medicament and a sterile air adjunct.

BRIEF DESCRIPTION OF THE DRAWINGS

The objects, features and advantages of the invention will be apparent to those skilled in the art from the following detailed description, taken together with the accompanying drawings, in which.

FIG. **5*b*** is a longitudinal section of the adjunct and the syringe, after sterile air has been withdrawn from the adjunct into the syringe.

FIG. **5*c*** is a longitudinal section of a multi-dose medicament vial and a syringe, after sterile air has been injected from the syringe into the vial.

FIG. **5*d*** is a longitudinal section of the vial and syringe, after a dose of medicament has been withdrawn from the vial into the syringe.

DETAILED DESCRIPTION OF THE INVENTION

Figure 4:
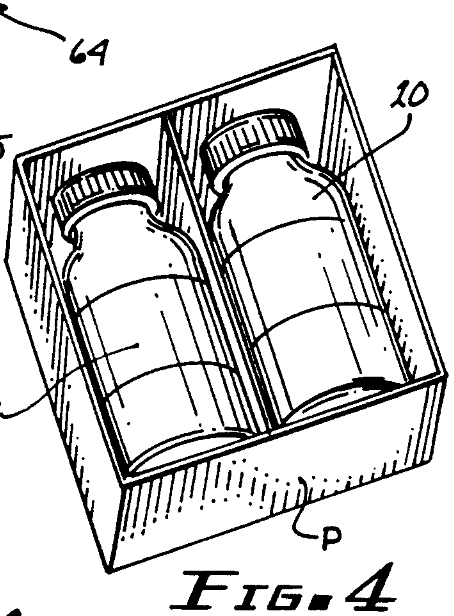
FIG. 4 is a perspective view of a tandem package containing a medicament vial and a sterile air adjunct FIG. **5*a*** is a longitudinal section of the medication injection adjunct of the present invention, together with an associated syringe, prior to withdrawal of sterile air from the adjunct.

The medication injection adjunct vessel may be in any suitable form or shape, although its preferred form is that of a cylinder or tube, with the aperture at one end. Several embodiments are shown, one in FIGS. 1 and 3, another in FIGS. **5*a* and 5*b*, and another in FIG. 4. In the embodiment of FIG. 4**, the vessel has the same configuration and size as that of the medicament vial with which it is packaged. The walls of the vessel are made of any suitable air impermeable material, such as glass, acrylic resin, or the like.

Figure 1:
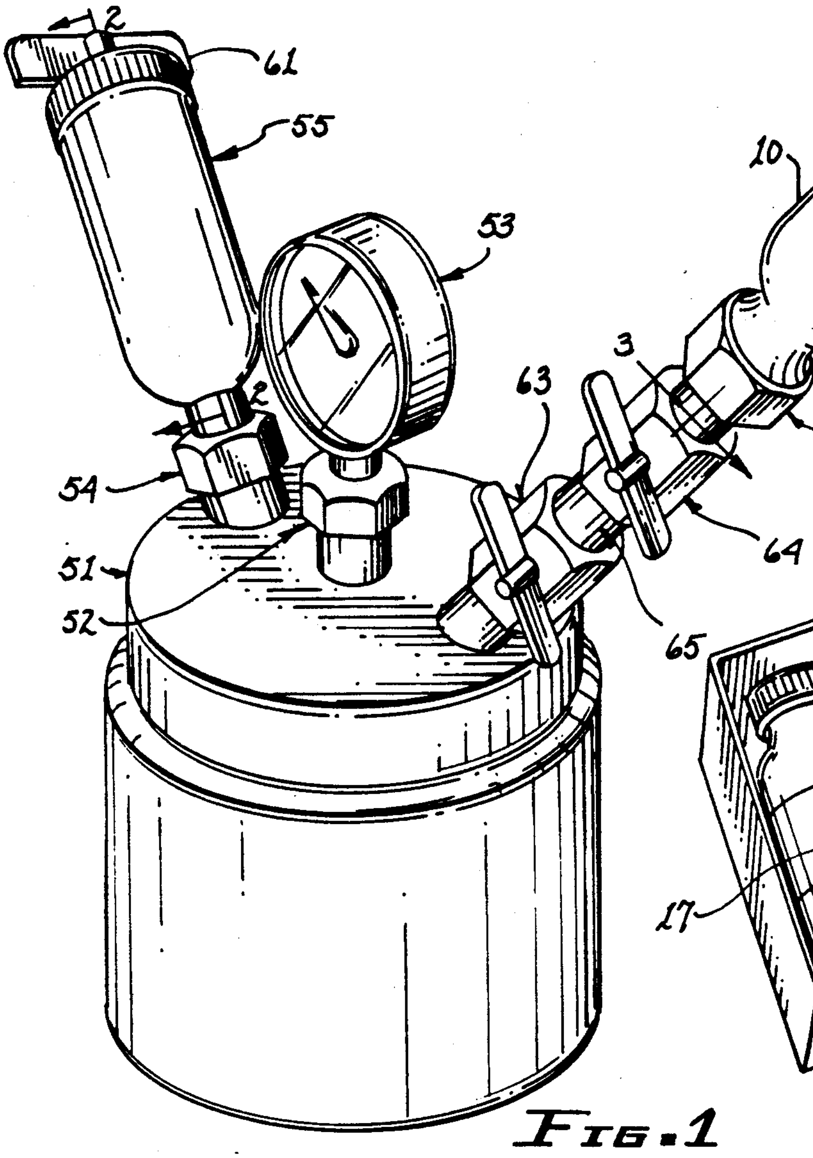
FIG. 1 is an elevation view of a portable pressurized storage vessel and associated low pressure sterile air dispensing adjunct.
Figure 3:
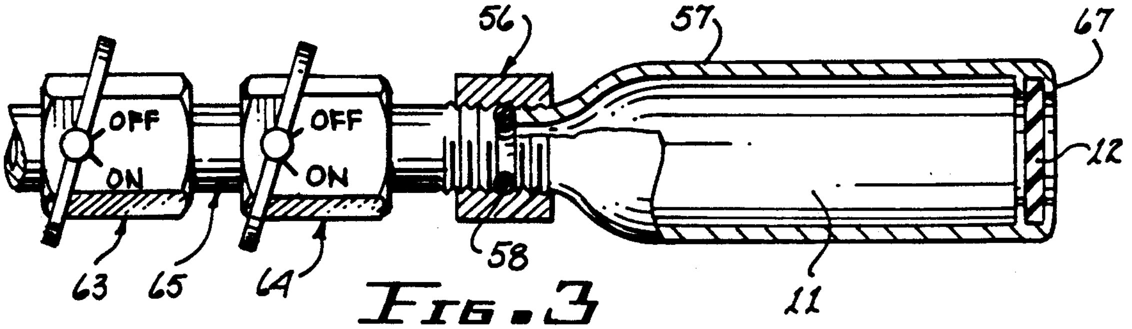
FIG. 3 is a cross section view of the associated sterile air dispensing adjunct, taken along the lines 3—3.
Figure 5A:
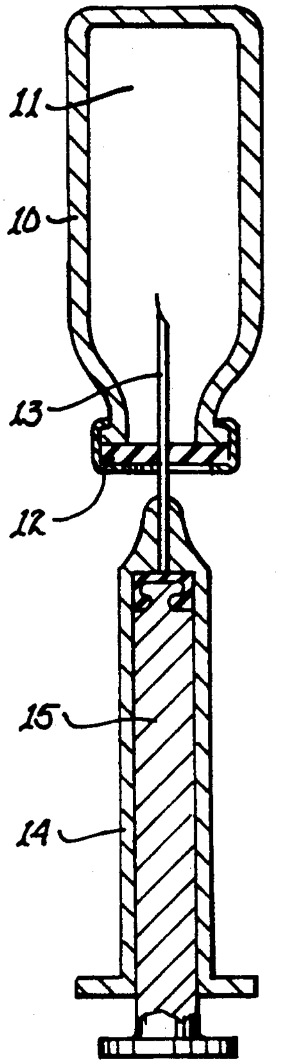
Figure 5E:
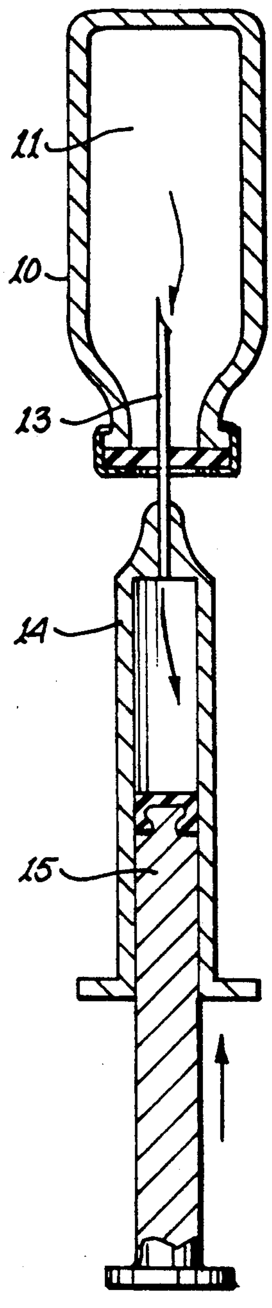
Figure 5C:
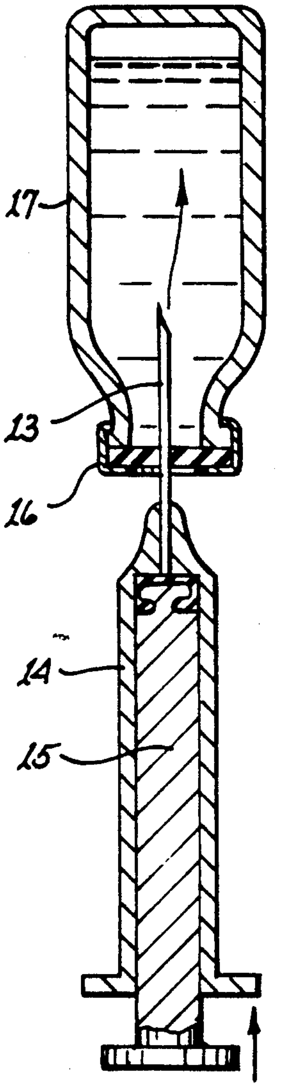
Figure 5D:
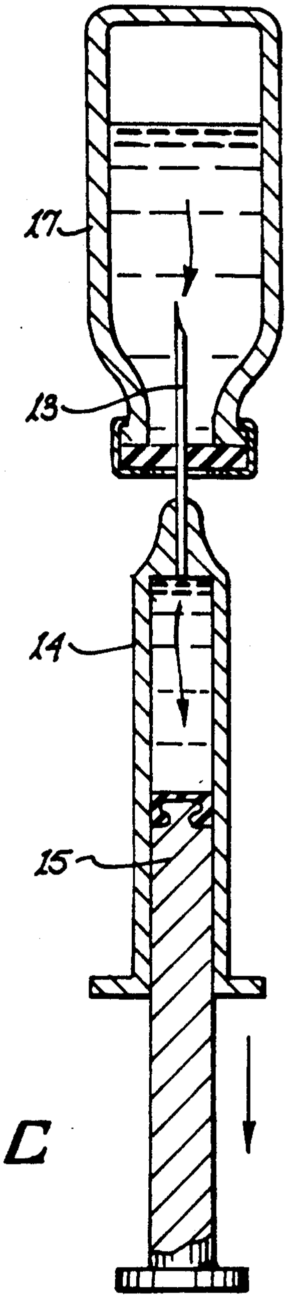

Referring to a preferred embodiment shown in FIGS. 1 and 3 of the drawings, the medicament injection adjunct of the present invention is a vessel 57 which contains sterile air 11 and which has an aperture at one end. The aperture is fitted with an air impermeable membrane or plug 12. The device thus comprises a closed vessel 57 filled with sterile air 11, with a septum 12 capable of being penetrated by the needle of a syringe.

Figure 2:
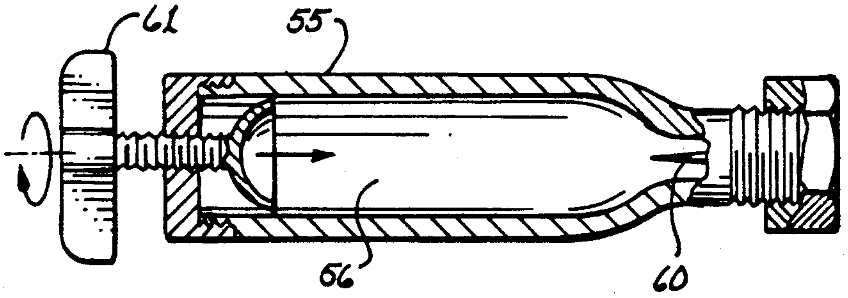
FIG. 2 is a cross section view, taken along the lines 2—2, of the compressed sterile air cylinder to be used with the storage vessel.

FIGS. 1-3 show the vessel 57 as part of apparatus including a portable sterile air storage container 50 fitted with a cap 51 which, if desired, can be made removable from container 50 by means of a threaded or clamping closure. In the embodiment shown in FIG. 1, cap 51 carries three separate connector outlets. The first is connector 52 which provides a means for attaching a pressure gauge 53. The second is connector 54, which provides a means for attaching a compressed air cylinder 55 (See FIG. 2). The third is connector 56 which provides means for attaching the sterile air dispensing adjunct vessel 57 (See FIG. 3). The connection between connector outlets 52, 54 and 56 and their associated items 53, 55 and 57 may be threaded or clamping means, or other known means for providing an airtight coupling. A typical coupling seal "O" ring 58 is shown in a cross section of connector 56.

The sterile air storage container 50 may be of any convenient size, such as 1 quart, 2 quart, 4 quart, etc. It is a feature of the invention that the cap 51 can be made to fit all sizes of container 50 used in the arrangement, thus facilitating manufacturing, inventorying and assembling procedures. The compressed air cylinder 55 is filled at the manufacturing plant with air which has been sterilized using known methods such as chemical, heat or the like.

In operation of the apparatus shown in FIGS. 1-3, the air pressure gauge 53 is attached to the coupling 52, the compressed air cartridge carrier 55 carrying air cylinder 56 is attached to coupling 54, and the sterile air adjunct 57 is attached to coupling 56. If the air pressure gauge 53 indicates that pressure in vessel 50 is low, the handle 61 on compressed air cartridge carrier 55 may be moved to advance air cartridge 56 which is punctured by needle 60 in a like manner as a $CO_2$ cartridge, for example, and open a one-way valve (not shown) to cause clean air to flow into container 50. If the air pressure in container 50 is sufficient, the valve 63 on coupling 56 may be opened to admit compressed air into the chamber 65 (which may be of any size suited to the purpose), then valve 63 is closed and valve 64 is opened to admit the measured value of compressed air from chamber 65 into the interior of vessel 57 to augment the pressure therein. A rubber closure 12 is located at the end 67 of adjunct 56.

In the alternative embodiment shown in FIGS. 5_a_ to 5_d_, the medicament injection adjunct 10 is initially filled with sterile air. The filling may be accomplished at the manufacturing site by charging the tube with air which has been sterilized by chemical means, heat treatment, or the like. It is a feature of the invention that the vessel 10 is filled with sterile air under pressure, so that repeated dose-size quantities can be withdrawn from the vessel before creating a vacuum condition which would resist further withdrawal of air. For example a 10 cc vessel containing sterile air under a pressure of about 1 or 2 oz. per cubic inch will allow withdrawal of a sufficient number of charges of air to be used in connection with the number of doses in a standard 10 cc medicament vial. The air pressure in the adjunct 10 should be greater than ambient pressure and may be adjusted, without undue experiment, to accommodate the size of the medicament vial with which it is to be used. In the case of medicament vials containing a large number of doses, it may not be possible to provide a corresponding number of charges of air with a single adjunct 10, since the required pressure may be more than the closure 12 can withstand, and in such cases it is contemplated that multiple adjunct units be available.

The operation of the invention to inject medication into a patient, is illustrated with reference to the alternative embodiment adjunct 10 shown in FIGS. 5_a_ to 5_d_; but the procedure is equally applicable to the preferred embodiment shown in FIGS. 1, 3 and 4. The aperture of the vessel 10 is fitted with an air impermeable closure 12. The preferred material for the closure is the standard rubber stopper currently used on multiple dose medicament vials. As in the case of the medicament vials, the closure 12 may comprise a rubber stopper or diaphragm, covered by a soft metal cap (e.g., aluminum), which is removed prior to use. In place of rubber, any other suitable material may be used if it is penetrable by the needle of a syringe and capable of preserving the seal after the syringe has been removed.

The outside surface of the closure 12 is cleansed with an alcohol pledget, and then, as shown in FIG. 1, the needle 13 of the syringe 14 is guided distally through the closure 12 to position the tip of the needle well within the interior of the adjunct 10. The relative positions of the adjunct 10 and the syringe 14 will then be as shown in FIG. 5_a_, with the plunger 15 still adjacent the distal end of the syringe barrel, ready to be moved proximally to withdraw air from the adjunct As to the next step, the plunger 15 is moved proximally to assume the position shown in FIG. 5_b_. Such movement causes sterile air to be withdrawn from the adjunct 10 and loaded into the barrel of the syringe 14. The movement of the plunger 15 should be sufficient to withdraw a volume of sterile air substantially equal to the volume of the medicament dose to be administered to the patient. As sterile air is drawn from the adjunct 10, pressure therein is lowered. However, since the adjunct is initially prepared under pressure, there will still be sufficient remaining pressure to make subsequent withdrawals available.

Next the outer surface of the rubber diaphragm 16 of a medicament vial 17 is cleansed with an alcohol pledget, and the needle 13 of the syringe 14 (which now contains only sterile air within its barrel) is guided distally through the rubber diaphragm 16 into the interior of vial 17. The plunger 15 of the syringe is then moved distally to expel the charge of sterile air into the interior of vial 17, thus increasing the air pressure within the vial. At this stage, the syringe 14 and the medicament vial 17 are positioned as shown in FIG. 5_c_.

Finally, the plunger 15 of the syringe 14 is moved proximally to the position shown in FIG. 5_d_, and in the course thereof a dose of liquid medicament is withdrawn from the vial 17 into the barrel of the syringe. The syringe is then removed from the vial, and the medicament is administered to the patient by injection through the skin.

In the embodiment of this invention shown in FIG. 4 a tandem medicament injection package is provided which contains a vial of medicament 17 and a companion sterile air adjunct 10 in a side by side package P.

Ideally, the adjunct 10 in FIG. 4 contains sterile air under sufficient pressure to provide a number of doses of air corresponding to the number of doses of medicament contained in vial 17. Some uses might require including one or more additional sterile air adjuncts in the tandem package.

The devices and method of the present invention provide the following features which are significantly advantageous in terms of effectiveness, safety and economics.

1. The necessary step of injecting air into a multiple dose medicament vial prior to withdrawing the medicament can now be carried out without introducing contaminated air through the skin of the patient.

2. The sterile air adjunct with which this is accomplished has a simple, uncomplicated, inexpensive structure which can be mass-produced on conventional machinery.

3. The simple, lightweight structure of the adjunct tube allows it to be packaged as a companion item with the medicament vial itself. The resulting tandem package thus furnishes not only the medicament but also a source for sterile air to be used for obtaining the medicament dose.

It will be understood that use of the term "sterile" herein contemplates not only conditions or materials which have been rendered completely aseptic but also those which have been treated to remove substantial proportions of microorganisms or other contaminants.

Although preferred embodiments of the invention have been described herein in detail, it will be understood by those skilled in the art that variations may be made thereto without departing from the spirit of the invention.

What is claimed is:

1. Apparatus comprising a container having a charge of sterile air under pressure, a medicament injection adjunct vessel, means communicating between the interior of said container and said vessel for transferring a measured value low pressure charge of sterile air from said container to said vessel, and means for closing said vessel after receiving said charge of sterile air from said container, said vessel having air impermeable walls and an aperture sealed by a puncturable, self-sealing closure.

2. The medicament injection adjunct of claim 1 wherein said closure is rubber.

3. The medicament injection adjunct of claim 1 wherein the walls of said vessel and container are an acrylic resin.

4. The medicament injection adjunct of claim 1 wherein the walls of said vessel and said container are glass.

5. The medicament injection adjunct of claim 1 wherein the pressure within said container is greater than about 1 oz. per square inch and the pressure in said vessel is not more than about 3 oz. per square inch.

6. A tandem medicament injection package comprising a vial of injectable medicament and companion vial adjunct means comprising at least one vessel having a charge of sterile air under pressure greater than ambient, said vessel having air impermeable walls and an aperture, said aperture sealed by a puncturable, self-sealing closure through which the needle of a syringe may be inserted to withdraw said sterile air.

7. A method of administering liquid medication to a patient by injection through the skin, comprising the steps of loading sterile air into the barrel of a syringe, pushing the syringe needle distally through the septum of a medicament vial, expelling air from the barrel of said syringe into the interior of said vial, moving the syringe plunger proximally to withdraw the desired dosage of medicament from said vial, and injecting said dosage through the skin of said patient

8. The method of claim 7 wherein the volume of sterile air expelled from the barrel of said syringe into the interior of said vial is approximately equal to the volume of medicament to be withdrawn from said vial.

9. The method of claim 7 wherein the sterile air loaded into said syringe has been sterilized by chemical means.

10. The method of claim 7 wherein the sterile air loaded into said syringe has been sterilized by heat.

* * * * *